United States Patent
Löffler et al.

(10) Patent No.: US 6,833,129 B2
(45) Date of Patent: *Dec. 21, 2004

(54) AQUEOUS OR AQUEOUS-ALCOHOLIC BODY-CLEANSING COMPOSITIONS COMPRISING OLIGOESTERS

(75) Inventors: Matthias Löffler, Niedernhausen (DE); Vera Mulitze-Kleinheyer, Frankfurt am Main (DE)

(73) Assignee: Clariant GmbH, Frankfurt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/289,001

(22) Filed: Nov. 6, 2002

(65) Prior Publication Data

US 2003/0104957 A1 Jun. 5, 2003

Related U.S. Application Data

(63) Continuation of application No. 09/770,918, filed on Jan. 26, 2001, now abandoned.

(30) Foreign Application Priority Data

Jan. 26, 2000 (DE) .......................................... 100 03 137

(51) Int. Cl.[7] .............................. A61K 7/00; A61K 7/48; A61K 7/50; C11D 3/37
(52) U.S. Cl. ..................... 424/70.11; 510/119; 510/130; 510/158; 510/159; 510/299; 510/342; 510/361; 510/434; 510/476; 510/479; 510/488; 510/533
(58) Field of Search ................................ 510/119, 130, 510/158, 159, 299, 342, 361, 434, 476, 479, 488, 533; 434/70.11; 134/39, 42

(56) References Cited

U.S. PATENT DOCUMENTS

| | | | |
|---|---|---|---|
| 4,116,885 A | 9/1978 | Derstadt et al. | ............ 252/532 |
| 4,711,730 A | 12/1987 | Gosselink et al. | ......... 252/8.75 |
| 4,785,060 A | 11/1988 | Nagler | ........................ 525/444 |
| 5,104,645 A | 4/1992 | Cardin et al. | .................. 424/70 |
| 5,142,020 A | 8/1992 | Kud et al. | .................... 528/272 |
| 5,612,307 A | 3/1997 | Chambers et al. | .......... 510/406 |
| 6,426,063 B1 * | 7/2002 | Schuler | .................... 424/70.11 |
| 6,489,395 B2 * | 12/2002 | Löffler | ......................... 524/845 |
| 2002/0006882 A1 * | 1/2002 | Loffler et al. | ............... 510/130 |
| 2003/0104957 A1 * | 6/2003 | Loffler et al. | ............... 510/130 |

FOREIGN PATENT DOCUMENTS

| | | |
|---|---|---|
| DE | 28 57 292 | 2/1980 |
| DE | 33 25 258 | 1/1985 |
| DE | 198 54 352 | 5/2000 |
| EP | 0 241 985 | 10/1987 |
| EP | 0 253 567 | 1/1988 |
| EP | 0 272 033 | 6/1988 |
| EP | 0 442 101 | 8/1991 |
| EP | 0 763 354 | 3/1997 |
| FR | 2 760 643 | 9/1998 |
| FR | 2 781 233 | 1/2000 |
| GB | 2 123 848 | 2/1984 |
| WO | WO 94/03152 | 2/1994 |
| WO | WO 97/26854 | 7/1997 |

OTHER PUBLICATIONS

XP–002169316, Chemial abstract, vol. 130, Apr. 1, 1999.
English abstract for FR 2760643, Sep. 18, 1998.
English abstract for FR 2781233, Jan. 21, 2000.
English abstract for DE 3325258, Jan. 24, 1985.

* cited by examiner

*Primary Examiner*—Brian P. Mruk
(74) *Attorney, Agent, or Firm*—Richard P. Silverman

(57) ABSTRACT

Body-cleansing compositions are claimed which comprise oligoesters obtained by condensation of one or more dicarboxylic acids or esters thereof and one or more polyhydric alcohols.

15 Claims, No Drawings

AQUEOUS OR AQUEOUS-ALCOHOLIC BODY-CLEANSING COMPOSITIONS COMPRISING OLIGOESTERS

CROSS-REFERENCES TO RELATED APPLICATIONS

This application is a continuation of U.S. application Ser. No. 09/770,918, flied Jan. 26, 2001, now abandoned, which is hereby incorporated by reference.

BACKGROUND OF THE INVENTION

The invention relates to aqueous or aqueous-alcoholic body-cleansing compositions for the mild cleansing and care of the skin, characterized by a content of oligoesters, comprising dicarboxylic acid units and diol units (glycol, alkylglycol and/or polyalkylene polyglycol units).

Body-cleansing and body care in two steps is time-consuming, meaning that many consumers prefer compositions with a combined cleansing and care action.

A large number of cosmetic products attempt to satisfy this demand.

U.S. Pat. No. 5,612,307 claims aqueous, liquid body-cleansing compositions which, in addition to customary surfactant systems, comprise a care component from the group of silicone oils, fats, oils, waxes, hydrophobic plant extracts, fatty acids, alcohols, esters, lipids and/or phospholipids.

WO 94/03152 claims shower gels consisting essentially of a surfactant, silicone oil and a cationic polymer.

One unsatisfactory aspect is that care and moisture-donating compounds cannot be incorporated into aqueous cleanser formulations in a sufficient amount. A further problem is that aqueous dispersions of surfactant systems and moisture-donating and care components separate over the course of time and are therefore not very storage-stable.

SUMMARY OF THE INVENTION

The object was therefore to develop novel skincare body-cleansing compositions which combine cleansing and care action and which are free from the abovementioned disadvantages.

The invention provides aqueous or aqueous-alcoholic body-cleansing compositions, with the exception of hair-treatment compositions, comprising oligoesters obtained by condensation of one or more dicarboxylic acids or esters thereof and one or more polyhydric alcohols.

DESCRIPTION OF THE PREFERRED EMBODIMENTS

These oligoesters are preferably obtained by polycondensation of one or more aromatic dicarboxylic acids or esters thereof with ethylene glycol and/or propylene glycol. Optionally, these esters may also contain polyethylene glycol, polypropylene glycol, sulfoisophthalic acid, sulfobenzoic acid, isethionic acid, $C_1$–$C_4$-alcohols, oxalkylated $C_1$–$C_{24}$-alcohols, oxalkylated $C_6$–$C_{18}$-alkylphenols and/or oxalkylated $C_8$–$C_{24}$-alkylamines as monomers.

Particular preference is given to the use of those oligoesters obtained by polycondensation of a) 40 to 52 mol %, preferably 45 to 50 mol %, of one or more aromatic dicarboxylic acids or esters thereof,
b) 10 to 40 mol %, preferably 20 to 35 mol %, of ethylene glycol and/or propylene glycol,
c) 3 to 20 mol %, preferably 10 to 15 mol %, of polyethylene glycol,
d) 0 to 10 mol % of a water-soluble addition product of from 5 to 89 mol of an alkylene oxide with 1 mol of $C_1$–$C_{24}$-alcohols, $C_6$–$C_{18}$-alkylphenols or $C_8$–$C_{24}$-alkylamines and
e) 0 to 10 mol % of one or more polyols having 3 to 6 hydroxyl groups.

Suitable as component a) for the preparation of the copolyesters are, for example, terephthalic acid, phthalic acid, isophthalic acid, and the mono- and dialkyl esters with $C_1$–$C_6$-alcohols, such as dimethyl terephthalate, diethyl terephthalate and di-n-propyl terephthalate. Further examples of compounds which may be used as component a) for the preparation of the polyesters are oxalic acid, succinic acid, glutaric acid, adipic acid, fumaric acid, maleic acid, itaconic acid, and the mono- and dialkyl esters of the carboxylic acids with $C_1$–$C_6$-alcohols, e.g. diethyl oxalate, diethyl succinate, diethyl glutarate, methyl adipate, diethyl adipate, di-n-butyl adipate, ethyl fumarate and dimethyl maleate. If the dicarboxylic acids which are suitable are able to form anhydrides, the anhydrides of the carboxylic acids having at least 2 carboxyl groups are also suitable as compound of component a) for the preparation of the oligoesters, e.g. maleic anhydride, phthalic anhydride or succinic anhydride. As compound of component a), particular preference is given to using terephthalic acid, phthalic acid, isophthalic acid, and the dimethyl, diethyl, dipropyl and dibutyl esters thereof. It is of course possible to use mixtures of different carboxylic acids or different esters. It is likewise also possible, for example, to use mixtures of carboxylic acids and esters, or mixtures of carboxylic acids and anhydrides in the condensation.

As component c), polyethylene glycols having molar masses of from 500 to 5000, preferably from 1000 to 3000, are used.

Suitable as component d) for the preparation of the oligoesters are water-soluble addition products of from 5 to 80 mol of at least one alkylene oxide with 1 mol of $C_1$–$C_{24}$-alcohols, $C_6$–$C_{18}$-alkylphenols or $C_8$–$C_{24}$-alkylamines. Preference is given to monomethyl ethers of polyethylene glycols. As alkylene oxides for the preparation of the compounds of component d), preference is given to using ethylene oxide, and mixtures of ethylene oxide and propylene oxide. Also suitable are mixtures of ethylene oxide together with propylene oxide and/or butylene oxide, mixtures of ethylene oxide, propylene oxide and isobutylene oxide, or mixtures of ethylene oxide and at least one butylene oxide. These water-soluble addition products of alkylene oxides are surfactants. If mixtures of alkylene oxides have been used for their preparation, then they may contain the alkylene oxides in blocks or also in random distribution.

Suitable alcohols which are alkoxylated are, for example, octyl alcohol, decyl alcohol, lauryl alcohol, myristyl alcohol or stearyl alcohol, but in particular methanol, and the alcohols having 8 to 24 carbon atoms obtainable by the Ziegler process, or the corresponding oxo alcohols. Of the alkylphenols, octylphenol, nonylphenol and dodecylphenol are of particular importance. Of the suitable alkylamines, use is made in particular of the $C_{12}$–$C_{18}$-monoalkylamines. Suitable as polyols (component e) are, for example, pentaerythritol, trimethylolethane, trimethylolpropane, 1,2,3-hexanetriol, sorbitol, mannitol and glycerol.

The oligoesters according to the invention are synthesized by processes known per se, by heating components a, b and c, and optionally d and e, with the addition of a catalyst, firstly at atmospheric pressure to temperatures of from 160 to about 220° C. The reaction is then continued under reduced pressure at temperatures of from 160 to about 240° C. with removal of excess glycols by distillation. The known transesterification and condensation catalysts of the prior art are suitable for the reaction such as, for example, titanium tetraisopropoxide, dibutyltin oxide and/or antimony trioxide/calcium acetate. For further details on carrying out the process, reference is made to EP 442 101.

Also suitable are the polyesters known from EP 241 985 which, in addition to oxyethylene groups and terephthalic acid units, contain 1,2-propylene, 1,2-butylene and/or 3-methoxy-1,2-propylene groups, and glycerol units and are terminally capped with $C_1$–$C_4$-alkyl groups, the soil release polymers described in EP 253 567 having a molar mass of from 900 to 9000 g/mol of ethylene terephthalate and polyethylene oxide terephthalate, where the polyethylene glycol units have molecular weights of from 300 to 3000 g/mol and the molar ratio of ethylene terephthalate to polyethylene oxide terephthalate is 0.6 to 0.95, and the polyesters containing polypropylene terephthalate and polyoxyethylene terephthalate units known from EP 272 033 and terminally capped at least proportionately by $C_1$–$C_4$-alkyl or acyl radicals.

Likewise preferred are oligoesters of ethylene terephthalate and polyethylene oxide terephthalate in which the polyethylene glycol units have molecular weights of from 750 to 5000 g/mol and the molar ratio of ethylene terephthalate to polyethylene oxide terephthalate is 50:50 to 90:10, and the use of which in detergents is described in German Patent DE 28 57 292, and oligoesters having molecular weights of from 15,000 to 50,000 g/mol of ethylene terephthalate and polyethylene oxide terephthalate, where the polyethylene glycol units have molecular weights of from 1000 to 10,000 g/mol and the molar ratio of ethylene terephthalate to polyethylen oxide terephthalate is 2:1 to 6:1 which, according to DE 33 24 258, can be used in detergents.

Also preferred are the oligoesters described in DE 19 644 034 of the formula

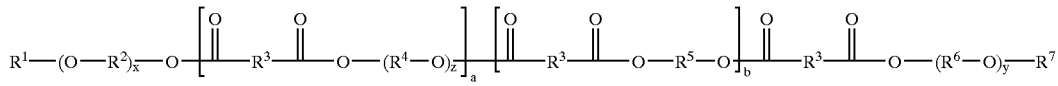

in which $R^1$ and $R^7$ are linear or branched $C_1$–$C_{18}$-alkyl,
$R^2$ and $R^6$ are ethylene,
$R^3$ is 1,4-phenylene,
$R^4$ is ethylene,
$R^5$ ethylene, 1,2-propylen or random mixtures of any composition of the two, x and y independently of one another are numbers between 1 and 500,
z is a number between 10 and 140,
a is a number between 1 and 12,
b is a number between 7 and 40,
where a+b is at least equal to 11.

Preferably, independently of one another, $R^1$ and $R^7$ are linear or branched $C_1$–$C_4$-alkyl,
x and y are numbers between 3 and 45,
z is a number between 18 and 70,
a is a number between 2 and 5,
b is a-number between 8 and 12,
a+b is a number between 12 and 18 or between 25 and 35.

The oligoesters described in DE 19 644 034 are obtained from dimethyl terephthalate, ethylene and/or propylene glycol, polyethylene glycol and $C_1$–$C_{18}$-alkylpolyethylene glycol with the addition of a catalyst firstly by esterification at temperatures of from 160 to about 220° C. and distillative removal of the methanol at atmospheric pressure and subsequent distillative removal of the excess glycols at temperatures of from 160 to about 240° C.

The oligoesters described are usually present in the aqueous or aqueous-alcoholic skin-cleansing compositions according to the invention in amounts of from 0.1 to 10% by weight, preferably 0.3 to 7% by weight, particularly preferably 2 to 5% by weight, based on the finished composition. The alcohols used are preferably ethanol and isopropanol. These skin-cleansing compositions are generally not in the form of oil-in-water or water-in-oil emulsions.

The skin-cleansing products according to the invention, for example shower preparations, shower gels, foam baths, comprising said oligoesters or mixtures of oligoesters can be combined with all customary anionic, cationic, zwitterionic, nonionic and amphoteric surfactants in aqueous or aqueous-alcoholic medium. The total amount of surfactants used in the compositions according to the invention can be between 5 and 70% by weight, preferably between 10 and 40% by weight, particularly preferably between 12 and 35% by weight, based on the finished composition.

Anionic washing-active substances which may be mentioned are: $C_{10}$–$C_{20}$-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkanesulfonates and hydroxyalkanesulfonates, olefinsulfonates, acyl esters of isethionates, α-sulfo fatty acid esters, alkylbenzenesulfonates, alkylphenol glycol ether sulfonates, sulfosuccinates, sulfosuccinic monoesters and diesters, fatty alcohol ether phosphates, protein/fatty acid condensation products, alkyl monoglyceride sulfates and sulfonates, alkyl glyceride ether sulfonates, fatty acid methyltaurides, fatty acid sarcosinates, sulforicinoleates, acyl glutamates. The compounds and mixtures thereof are used in the form of their water-soluble or water-dispersible salts, for example sodium, potassium, magnesium, ammonium, mono-, di- and triethanolammonium, and analogous alkylammonium salts.

The proportion by weight of the anionic surfactants in the compositions according to the invention is in the range from 7 to 30%, preferably 10 to 25%, particularly preferably 12 to 22%.

Suitable cationic surfactants are, for example, quaternary ammonium salts, such as di($C_{10}$–$C_{24}$-alkyl)dimethylammonium chloride or bromide, preferably di($C_{12}$–$C_{18}$-alkyl)-dimethylammonium chloride or bromide; $C_{10}$–$C_{24}$-alkyldimethylethylammonium chloride or bromide; $C_{10}$–$C_{24}$-alkyltrimethylammonium chloride or bromide, preferably cetyltrimethylammonium chloride or bromide and $C_{20}$–$C_{22}$-alkyltrimethylammonium chloride or bromide; $C_{10}$–$C_{24}$-alkyldimethylbenzylammonium chloride or bromide, preferably $C_{12}$–$C_{18}$-alkyldimethylbenzylammonium chloride; N-($C_{10}$–$C_{18}$-alkyl)-pyridinium chloride or bromide, preferably N-($C_{12}$–$C_{16}$-alkyl)pyridinium chloride or bromide; N-($C_{10}$–$C_{18}$-alkyl)isoquinolinium chloride, bromide or monoalkylsulfate; N-($C_{12}$–$C_{18}$-alkylpolyolaminoformylmethyl)pyridinium chloride; N-($C_{12}$–$C_{18}$-alkyl)-N-methylmorpholinium chloride, bromide or monoalkylsulfate; N-($C_{12}$–$C_{18}$-alkyl)-N-ethylmorpholinium chloride, bromide or monoalkylsulfate; $C_{16}$–$C_{18}$-alkylpentaoxethylammonium chloride;

diisobutylphenoxyethoxyethyl-dimethylbenzylammonium chloride; salts of N,N-diethylaminoethylstearylamide and -oleylamide with hydrochloric acid, acetic acid, lactic acid, citric acid, phosphoric acid; N-acylaminoethyl-N,N-diethyl-N-methylammonium chloride, bromide or monoalkylsulfate and N-acylaminoethyl-N,N-diethyl-N-benzylammonium chloride, bromide or monoalkylsulfate, where acyl is preferably stearyl or oleyl.

The proportion by weight of the cationic surfactants in the compositions according to the invention is in the range from 1 to 10%, preferably 2 to 7%, particularly preferably 3% to 5%.

Examples of suitable nonionic surfactants which may be used as washing-active substrances are: fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols); polypropylene glycol ethoxylates (Pluronic); fatty acid alkylolamides, (fatty acid amide polyethylene glycols); N-alkyl-, N-alkoxypolyhydroxy fatty acid amides, sucrose esters; sorbitol esters and polyglycol ethers.

The proportion by weight of the nonionic surfactants in the compositions according to the invention is in the range from 1 to 20%, preferably 2 to 10%, particularly preferably 3 to 7%.

Preferred amphoteric surfactants are: N-($C_{12}$–$C_{18}$-alkyl)-β-aminopropionates and N-($C_{12}$–$C_{18}$-alkyl)-β-iminodipropionates as alkali and mono-, di- and trialkylammonium salts; N-acylaminoalkyl-N,N-dimethylacetobetaine, preferably N-($C_8$–$C_{18}$-acyl) aminopropyl-N,N-dimethylacetobetaine; $C_{12}$–$C_{18}$-alkyldimethylsulfopropylbetaine; amphoteric surfactants based on imidazoline (trade name: Miranol®, Steinapon®), preferably the sodium salt of 1-(β-carboxymethyloxyethyl)-1-(carboxymethyl)-2-laurylimidazolinium; amine oxides, e.g. $C_{12}$–$C_{18}$-alkyldimethylamine oxide, fatty acid amidoalkyldimethylamine oxide.

The proportion by weight of the amphoteric surfactants in the compositions according to the invention is in the range from 0.5 to 20%, preferably 1 to 10%.

In addition, foam-enhancing cosurfactants from the group alkylbetaines, alkylamidobetaines, aminopropionates, aminoglycinates, imidazoliniumbetaines and sulfobetaines, amine oxides and fatty acid alkanolamides or polyhydroxyamides may be used in the compositions according to the invention.

Preferred surfactants in the compositions according to the invention are lauryl sulfate, laureth sulfate, cocoamidopropylbetaine, sodium cocoyl glutamate, disodium laureth sulfosuccinate and coconut fatty acid diethanolamide.

The preparations according to the invention can also comprise further additives customary in cosmetics, such as superfatting agents, stabilizers, biogenic active ingredients, glycerol, preservatives, pearlizing agents, dyes and fragrances, solvents, opacifiers, thickeners and dispersants, and also protein derivatives, such as gelatin, collagen hydrolyzates, polypeptides on a natural and synthetic basis, egg yolk, lecithin, lanolin and lanolin derivatives, fatty alcohols, silicones, deodorizing agents, substances having keratolytic and keratoplastic action, enzymes and carrier substances. Furthermore, antimicrobially acting agents may be added to the compositions according to the invention.

Superfatting agents which may be used are, for example, polyethoxylated lanolin derivatives, lecithin derivatives, polyol fatty acid esters, monoglycerides and fatty acid alkanolamides, the latter also serving as foam stabilizers. Typical examples of fats are glycerides, and suitable waxes are, inter alia, beeswax, paraffin wax or microcrystalline waxes, optionally in combination with hydrophilic waxes, e.g. cetylstearyl alcohol.

Stabilizers which may be used are metal salts of fatty acids, such as e.g. magnesium stearate, aluminum stearate and/or zinc stearate. Biogenic active ingredients are understood as meaning, for example, plant extracts and vitamin complexes.

Suitable preservatives are, for example, phenoxyethanol, formaldehyde solution, parabens, pentanediol or sorbic acid. Suitable pearlizing agents are, for example, glycol distearic esters, such as ethylene glycol distearate, but also fatty acid monoglycol esters.

Dyes which may be used are the substances approved and suitable for cosmetic purposes.

Suitable thickeners are sodium chloride, potassium chloride, ammonium chloride, sodium sulfate, fatty acid alkylolamides, cellulose derivatives, for example hydroxyethylcellulose, guar gum, polyvinyl alcohol, polyvinylpyrrolidone, hydroxypropyl guar gum, starch and starch derivatives, and natural gums, carboxyvinyl polymers, for example Carbopol 934, 940, 941, 956, 980, 981, 1342 and 1382.

Particularly suitable as thickeners and dispersants are ethylene glycol esters of fatty acids having 14 to 22 carbon atoms, particularly preferably 16 to 22 carbon atoms, in particular mono- and diethylene glycol stearate. Preference is also given to stearin monoethanolamide, stearin diethanolamide, stearin isopropanolamide, stearin monoethanolamide stearate, stearyl stearate, cetyl palmitate, glyceryl stearate, stearamide diethanolamide distearate, stearamide monoethanolamide stearate, N,N-dihydrocarbyl ($C_{12}$–$C_{22}$, in particular $C_{16}$–$C_{18}$)-amidobenzoic acid and soluble salts thereof, N,N-di($C_{16}$–$C_{18}$)amidobenzoic acid and derivatives.

The dispersants are used in concentrations of from 0.5 to 10% by weight, preferably from 0.5 to 5% by weight, particularly preferably from 1 to 4% by weight, based on the finished composition.

The desired viscosity of the compositions may be adjusted by adding water and/or organic solvents or by adding a combination of organic solvents and thickeners.

In principle, suitable organic solvents are all monohydric or polyhydric alcohols. Preference is given to using alcohols having 1 to 4 carbon atoms, such as ethanol, propanol, isopropanol, n-butanol and isobutanol, glycerol and mixtures of said alcohols. Further preferred alcohols are polyethylene glycols with a relative molecular mass below 2000. In particular, use of polyethylene glycol with a relative molecular mass between 200 and 600 and in amounts up to 45% by weight and of polyethylene glycol with a relative molecular mass between 400 and 600 in amounts of from 5 to 25% by weight is preferred. Further suitable solvents are, for example, triacetin (glycerol triacetate) and 1-methoxy-2-propanol.

Suitable carrier materials are vegetable oils, natural and hydrogenated oils, waxes, fats, water, alcohols, polyols, glycerol, glycerides, liquid paraffins, liquid fatty alcohols, sterol, polyethylene glycols, cellulose and cellulose derivatives.

Fungicidal active ingredients which may be used are ketoconazole, oxiconazole, terbinafine, bifonazole, butoconazole, cloconazole, clotrimazole, econazole, enilconazole, fenticonazole, isoconazole, miconazole, sulconazole, tioconazole and fluconazole, itraconazole, terconazole and naftifine.

In order to be able to improve the affinity of the oligoester (s) used according to the invention on the skin, cationic guar polymers may be used in the amounts by weight of from 0.01 to 1.0%, preferably 0.02 to 0.25%, as described in WO 97/26854.

Silicones, polyalkylsiloxanes, polyalkylarylsiloxanes, polyether siloxane copolymers, as described in U.S. Pat. No. 5,104,645 and publications cited therein further improve the care action of the compositions according to the invention. The compositions according to the invention can be admixed with conventional ceramides, pseudoceramides, fatty acid N-alkylpolyhydroxyalkylamides, cholesterol, cholesterol fatty acid esters, fatty acids, triglycerides, cerebrosides, phospholipids and similar substances.

The compositions according to the invention are prepared in a manner known per se by combining the individual components and, if required, further processing them in a manner appropriate for the particular type of preparation. Some of these possible diverse preparation forms are described by way of example in the working examples.

Use according to the invention of polyesters in aqueous or aqueous-alcoholic body-cleansing compositions, in particular in shower preparations, shower gels and foam baths, allows skin damage to be avoid, and the nature of the foam and the skin friendliness of the composition to be improved.

The examples below serve to illustrate the subject-matter of the invention in more detail, without limiting it thereto.

EXAMPLES

Example 1

Shower Gel

| | Component | % by weight |
|---|---|---|
| 1 | PEG-120 methyl glucose dioleate | 1.25 |
| 2 | Polyquaternium-10 | 0.3 |
| 3 | Glycerol | 2.0 |
| 4 | Polyester 1 | 2.0 |
| 5 | Coconut fatty acid | 2.0 |
| 6 | Genagen LDA | 6.2 |
| 7 | Genagen CAB | 3.0 |
| 8 | Hostapon CLG | 3.6 |
| 9 | Citric acid 25% | 1.05 |
| 10 | Methyldibromoglutaronitrile/phenoxyethanol | 0.05 |
| 11 | Perfume | 0.5 |
| 12 | Genapol TSM | 4.0 |
| 13 | Demineralized water | ad 100 |

Components 1, 2, 4 and 5 were initially introduced and dissolved in demineralized water at about 70° C. with stirring. 6, 7, 8 and 3 were added one after the other with stirring, and the pH was adjusted to pH 6.0 with citric acid. By adding 10 and 11, the composition was preserved and perfumed, and provided with the opacifier 12.

Example 2

Shower Preparation

| | Component | % by weight |
|---|---|---|
| 1 | PEG-120 methyl glucose dioleate | 1.25 |
| 2 | Polyquaternium-10 | 0.3 |
| 3 | Glycerol | 2.0 |
| 4 | Polyester 3 | 2.0 |
| 5 | Coconut fatty acid | 2.0 |
| 6 | Genapol LRO | 14.0 |
| 7 | Genagen LDA | 1.9 |
| 8 | Genagen CAB | 1.0 |
| 9 | Hostapon CLG | 1.0 |
| 10 | Citric acid 25% | 1.05 |
| 11 | Methyldibromoglutaronitrile/phenoxyethanol | 0.05 |
| 12 | Perfume | 0.5 |

-continued

| | Component | % by weight |
|---|---|---|
| 13 | Titanium dioxide | 0.2 |
| 14 | Demineralized water | ad 100 |

Components 1, 2, 4 and 5 were initially introduced and dissolved in demineralized water at about 70° C. with stirring. 6, 7, 8, 9 and 3 were added one after the other with stirring, and the pH was adjusted to pH 6.1 with citric acid. By adding 11 and 12, the composition was preserved and perfumed, and provided with the opacifier 13.

Example 3

Shower Preparation

| | Component | % by weight |
|---|---|---|
| 1 | PEG-120 methyl glucose dioleate | 2.25 |
| 2 | Polyquaternium-10 | 0.3 |
| 3 | Glycerol | 2.0 |
| 4 | Polyester 2 | 5.0 |
| 5 | Coconut fatty acid | 2.0 |
| 6 | Medialan LD | 2.0 |
| 7 | Genapol LRO | 3.15 |
| 8 | Genagen LDA | 5.4 |
| 9 | Genagen CAB | 3.0 |
| 10 | Hostapon CLG | 3.6 |
| 11 | Citric acid 25% | 1.05 |
| 12 | Methyldibromoglutaronitrile/phenoxyethanol | 0.05 |
| 13 | Perfume | 0.5 |
| 14 | Sodium-styrene-acrylate copolymer/sodium lauryl sulfate/trideceth-7 | 0.8 |
| 15 | Demineralized water | ad 100 |

Components 1, 2, 4 and 5 were initially introduced and dissolved in demineralized water at about 70° C. with stirring. 6, 7, 8, 9, 10 and 3 were added one after the other with stirring, and the pH was adjusted to pH 6.2 with citric acid. By adding 12 and 13 the composition was preserved and perfumed, and provided with the opacifier 14.

Chemical names of the commercial products used

| | |
|---|---|
| Genapol TSM | PEG-3 distearates/sodium laureth sulfate |
| Genagen LDA | Lauroamphodiacetate, sodium salt |
| Genagen CAB | Cocamidopropylbetaine |
| Hostapon CLG | Lauroyl glutamate, sodium salt |
| Medialan LD | Lauroyl sarcosinate, sodium salt |
| Genapol LRO | Laureth sulfate, sodium salt |
| Polyester 1 | about 40 mol % of terephthalic acid, |
| | about 10 mol % of ethylene glycol, |
| | about 10 mol % of propylene glycol |
| | about 20 mol % of polyethylene glycol |
| | about 10 mol % of fatty alcohol ethoxylate |
| | about 10 mol % of polyol |
| Polyester 2 | about 50 mol % of terephthalic acid, |
| | about 25 mol % of ethylene glycol, |
| | about 20 mol % of polyethylene glycol |
| | about 5 mol % of fatty alcohol ethoxylate |

-continued

| Polyester 3 | about 50 mol % of hexanedioic acid<br>about 40 mol % of propylene glycol,<br>about 10 mol % of polyethylene glycol |
|---|---|

What is claimed is:

1. A method for cleansing human skin comprising treating the human skin with an aqueous or aqueous-alcoholic body-cleansing composition comprising oligoesters obtained by condensation of one or more dicarboxylic acids or esters thereof and one or more polyhydric alcohols, wherein said body-cleansing composition further comprises from 5 to 70% by weight of surfactants based on a finished composition and said body-cleansing composition being neither a water-in-oil or oil-in-water emulsion forming a foam.

2. The method of claim 1, wherein said body-cleansing composition comprises oligoesters obtained by polycondensation of one or more dicarboxylic acids or esters thereof and ethylene glycol and/or propylene glycol, and optionally a compound selected from the group consisting of polypropylene glycol, polyethylene glycol, sulfoisophthalic acid, sulfobenzoic acid, isethionic acid, $C_1$–$C_4$-alcohols, oxalkylated $C_1$–$C_2$alcohols, oxalkylated $C_6$–$C_{18}$-alkylphenols, oxalkylated $C_6$–$C_{24}$-alkyiamlnes, and mixtures thereof.

3. The method of claim 1, wherein said body-cleansing composition comprises oligoesters obtained by polycondensation of
a) 40 to 52 mol %, of one or more aromatic dicarboxylic acids or esters thereof,
b) 10 to 60 mol %, of ethylene glycol and/or propylene glycol,
c) 0 to 20 mol %, of polyethylene glycol,
d) 0 to 10 mol % of a water-soluble addition product of from 5 to 80 mol of an alkylene oxide with 1 mol of $C_1$–$C_{24}$-alcohols, $C_6$–$C_{18}$-alkylphenols or $C_6$–$C_{24}$-alkylamines and
e) 0 to 10 mol % of one or more polyols having 3 to 5 hydroxyl groups.

4. The method of claim 1, wherein said body cleansing composition comprises 0.1 to 5% by weight of said oligoesters.

5. A method according to claim 1 wherein said treating comprises a treatment comprising contacting the akin with a product selected from the group consisting of a shower preparation, a shower gel, and a foam bath.

6. The method of claim 1 wherein the dicarboxylic acids or esters thereof are aromatic dicarboxylic acids or esters thereof.

7. The method of claim 6 wherein the one or more aromatic dicarboxylic acids or esters thereof are selected from the group consisting of terephthalic acid, phthalic acid, isophthalic acid, and the dimethyl, diethyl, dipropyl, and dibutyl esters thereof.

8. The method of claim 1, wherein the one or more polyhydric alcohols are selected from the group consisting of ethylene glycol, propylene glycol, and mixtures thereof.

9. The method of claim 1 wherein said oligoesters are obtained by the condensation of terephthalic acid and polyethylene glycols wherein the polyethylene glycols have a molecular mass of from 500 to 5000.

10. The method of claim 1, wherein said body-cleansing composition comprises oligoesters obtained by polycondensation of
a) up to 52 mol %, of terephthalic acid or esters thereof,
b) 10 to 60 mol %, of ethylene glycol and/or propylene glycol,
c) 0 to 20 mol %, of polyethylene glycol,
d) 0 to 10 mol % of a water-soluble addition product of from 5 to 80 mol of an alkylene oxide with 1 mol of $C_1$–$C_{24}$-alcohols, $C_8$–$C_{18}$-alkylphenols or $C_8$–$C_{24}$-alkylamines and
e) 0 to 10 mol % of one or more polyols having 3 to 6 hydroxyl groups.

11. A method for cleansing human skin comprising treating the human skin with an aqueous or aqueous-alcoholic body-cleansing composition comprising oligoesters of the formula:

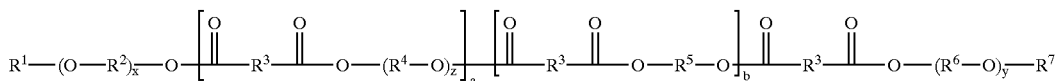

wherein
$R^1$ and $R^7$ are linear or branched $C_1$–$C_{18}$-alkyl,
$R^2$ and $R^8$ are ethylene,
$R^3$ is 1,4-phenylene,
$R^4$ is ethylene,
$R^6$ ethylene, 1,2-propylene or random mixtures of any composition of the two, x and y independently of one another are numbers between 1 and 500,
z is a number between 10 and 140,
a is a number between 1 and 12,
b is a number between 7 and 40,
and a+b at least equal to 11, wherein said body-cleansing composition further comprising from 5 to 70% by weight of surfactants based on a finished composition and said body-cleansing composition being neither a water-in-oil or oil-in-water emulsion forming a foam.

12. The method of claim 11 wherein independently of one another,
$R^1$ and $R^7$ are linear or branched $C^1$–$C^4$-alkyl,
x and y are numbers between 3 and 45,
z is a number between 18 and 70,
a is a number between 2 and 5,
b is a number between 8 and 12, and
a+b is a number between 12 and 18.

13. The method of claim 3, wherein said body-cleansing, composition comprises oligoesters obtained by polycondensation of 45 to 50 mol % of one or more aromatic dicarboxylic acids or esters.

14. The method of claim 3, wherein said body-cleansing composition comprises oligoesters obtained by polycondensation of 20 to 35 mol %, of ethylene glycol and/or propylene glycol.

15. The method of claim 3, wherein said body-cleansing composition comprises oligoesters obtained by polycondensation of 10 to 15 mol %, of polyethylene glycol.

* * * * *